United States Patent

Misslitz et al.

Patent Number: 5,674,812
Date of Patent: Oct. 7, 1997

[54] 5(SULFO-/CARBAMOYLMETHYL) CYCLOHEXENONE OXIME ETHERS

[75] Inventors: Ulf Misslitz, Neustadt; Helmut Walter, Obrigheim; Karl-Otto Westphalen, Speyer; Matthias Gerber, Limburgerhof, all of Germany

[73] Assignee: BASF Aktiengesellschaft, Ludwigshafen, Germany

[21] Appl. No.: 414,599

[22] Filed: Mar. 31, 1995

[30] Foreign Application Priority Data

Mar. 31, 1994 [DE] Germany ............... 44 11 249.1

[51] Int. Cl.$^6$ ............... A01N 33/24; A01N 33/08; C07C 251/50; C07C 251/52
[52] U.S. Cl. ............... 504/333; 504/339; 564/99; 564/219; 564/221
[58] Field of Search ............... 564/199, 339, 564/99, 219, 221, 333

[56] References Cited

FOREIGN PATENT DOCUMENTS

| | | |
|---|---|---|
| 456 068 | 11/1991 | European Pat. Off. |
| 456 069 | 11/1991 | European Pat. Off. |
| 456 089 | 11/1991 | European Pat. Off. |
| 456 112 | 11/1991 | European Pat. Off. |
| 456 118 | 11/1991 | European Pat. Off. |
| 38 38 309 | 5/1990 | Germany |
| 92/08696 | 5/1992 | WIPO |
| 93/10081 | 5/1993 | WIPO |
| 93/16033 | 8/1993 | WIPO |
| 93/16062 | 8/1993 | WIPO |

*Primary Examiner*—Peter O'Sullivan
*Attorney, Agent, or Firm*—Keil & Weinkauf

[57] ABSTRACT

5-(Sulfo-/carbamoylmethyl)cyclohexenone oxime ethers I

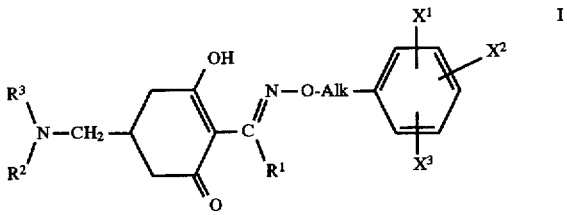

where
$R^1 = C_1-C_6$-alkyl;
$R^2 = $H, $C_1-C_6$-alkyl, $C_1-C_3$-alkoxy-$C_1-C_3$-alkyl, $C_3-C_6$-cycloalkyl;
$R^3 = C_1-C_4$-alkylsulfonyl or $C_1-C_4$-alkylcarbonyl;
Alk = a $C_2-C_4$-alkylene, $C_3-C_4$-alkenylene, $C_3-C_4$-alkynylene or $C_2-C_3$-alkyleneoxy chain, it being possible for each chain if desired to carry a $C_1-C_3$-alkyl group;
$X^1$, $X^2$ and $X^3 = $H, halogen, $C_1-C_4$-haloalkyl,
and their salts and esters are described.

7 Claims, No Drawings

5(SULFO-/CARBAMOYLMETHYL) CYCLOHEXENONE OXIME ETHERS

BACKGROUND OF THE INVENTION

1. Field of the Invention

The present invention relates to novel 5-(sulfo-/carbamoyl-methyl)cyclohexenone oxime ethers of the formula I

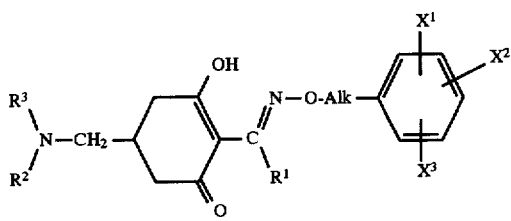

where the variables have the following meanings:

$R^1$ is $C_1$–$C_6$-alkyl;

$R^2$ is hydrogen, $C_1$–$C_6$-alkyl, $C_1$–$C_3$-alkoxy-$C_1$–$C_3$-alkyl or $C_3$–$C_6$-cycloalkyl;

$R^3$ is $C_1$–$C_4$-alkylsulfonyl or $C_1$–$C_4$-alkylcarbonyl;

Alk is a $C_2$–$C_4$-alkylene chain, a $C_3$- or $C_4$-alkenylene chain, a $C_3$- or $C_4$-alkynylene chain, a $C_2$- or $C_3$-alkyleneoxy chain, it being possible for each chain if desired to carry a $C_1$–$C_3$-alkyl group;

$X^1$, $X^2$ and $X^3$ independently of one another are hydrogen, halogen or $C_1$–$C_4$-haloalkyl, and the agriculturally utilizable salts of I and the esters of I with $C_1$–$C_{10}$-carboxylic acids or inorganic acids.

The invention additionally relates to the use of these compounds as herbicides, to herbicidal compositions which contain these compounds as active ingredients and to a method for controlling undesired plant growth using these herbicidal compositions.

2. Description of the Related Art

Herbicidally active cyclohexane diones of the formula IV

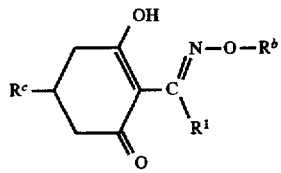

are already known from the literature, $R^b$ and $R^c$ having, inter alia, the following meanings:

DE-A 38 38 309 ($R^b$=a substituted 4-phenylbutylene or 4-phenylbutenylene radical; $R^c$=a substituted 5- to 7-membered heterocycle);

EP-A 456 068 ($R^b$=a substituted 4-phenylbutynylene radical; $R^c$=a substituted 5- to 7-membered heterocycle);

EP-A 456 112 ($R^b$=a substituted 3-phenoxypropylene or 2-phenoxyethylene radical; $R^c$=a substituted 5- to 7-membered heterocycle);

WO 92/08696 ($R^b$=substituted alkyl, alkenyl, alkinyl, benzyl; $R^c$=N-(alkylsulfonyl)-N-alkylaminoalkyl or N-(alkylcarbonyl)-N-alkylaminoalkyl).

In addition, WO 93/10081 describes herbicidally active cyclohexenone oxime ethers which, in the 5-position as defined, inter alia can carry an N-(alkylsulfonyl)-N-alkylaminoalkyl or N-(alkylcarbonyl)-N-alkylaminoalkyl group. Examples of compounds of this type and their herbicidal properties cannot be inferred, however, from this reference.

SUMMARY OF THE INVENTION

Since the herbicidal properties of the known compounds, in particular with respect to their selectivity to grass weeds in gramineous crop plants are not always completely satisfactory, the invention was based on novel cyclohexenone oxime ethers using which grass weeds in gramineous crops such as rice and maize can be specifically controlled better than hitherto.

Accordingly, the 5-(sulfo-/carbamoylmethyl) cyclohexenone oxime ethers I defined at the outset have now been found. Additionally, their use as herbicides, herbicidal compositions which contain the compounds I, and a method for controlling undesired plant growth using these compositions have been found.

DESCRIPTION OF THE PREFERRED EMBODIMENTS

The novel 5-(sulfo-/carbamoylmethyl)cyclohexenone oxime ethers I are obtainable in various ways, to be specific preferably in a manner known per se from already-known cyclohexenones of the formula II (cf. eg. WO 92/08696) and hydroxylamines of the formula III (cf. eg. DE-A 38 38 309, EP-A 456 068, EP-A 456 069, EP-A 456 089, EP-A 456 112 and WO 93/16033):

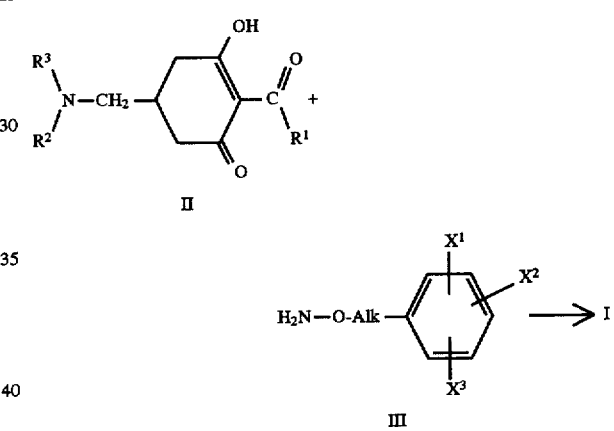

The hydroxylamine III is expediently employed as a suitable ammonium salt, in particular as the hydrochloride. The reaction in this case is advantageously carried out in a heterogeneous phase of water and a largely water-immiscible inert organic solvent.

Suitable organic solvents are preferably dimethyl sulfoxide, alcohols such as methanol, ethanol and isopropanol, aromatic hydrocarbons such as benzene and toluene, chlorinated hydrocarbons such as chloroform and 1,2-dichloroethane, aliphatic hydrocarbons such as hexane and cyclohexane, esters such as ethyl acetate or ethers such as diethyl ether, dioxane and tetrahydrofuran.

In this embodiment, the reaction is customarily carried out in the presence of a base, an amount of base of from approximately 0.5 to 2 mol equivalents, based on the hydroxylammonium salt, normally being sufficient.

Suitable bases are eg. carbonates, hydrogen carbonates, acetates, alkoxides or oxides of alkali metals or alkaline earth metals, in particular sodium hydroxide, potassium hydroxide, magnesium oxide and calcium oxide. In addition, organic bases such as pyridine and tert-amines such as triethylamine can be used.

Reaction in methanol using sodium hydrogen carbonate as a base has proven particularly advantageous.

The reaction can also be performed without base using the free hydroxylamine III; depending on the solvent used for the compound II, a single- or two-phase reaction mixture is obtained in this case.

Suitable solvents for this variant are, for example, alcohols such as methanol, ethanol, isopropanol and cyclohexanol, aliphatic and aromatic, unchlorinated or chlorinated hydrocarbons such as hexane, cyclohexane, methylene chloride, toluene and dichloroethane, esters such as ethyl acetate, nitriles such as acetonitrile and cyclic ethers such as dioxane and tetrahydrofuran.

Normally, the cyclohexenone II and the hydroxylamine III or its ammonium salt are employed in approximately stoichiometric amounts. To optimize the conversion, eg. of cyclohexenone II, it may, however, be advantageous to employ an excess of hydroxylamine III or its ammonium salt of up to about 30 mol %.

The reaction temperature is in general from 0° C. to the boiling point of the reaction mixture, preferably from 20° to 80° C.

Particular conditions with respect to the pressure need not be observed; in general the reaction is therefore carried out at normal pressure or under the autogenous pressure of the particular diluent.

The reaction mixtures obtained can be worked up to the products I by means of customary workup methods. To do this, the residue normally obtained after removal of the low-boiling fractions is first partitioned in methylene chloride/water. After removing the organic solvent under reduced pressure, the desired compound I is then obtained.

As a result of their acidic character, the 5-(sulfo-/carbamoylmethyl)cyclohexenone oxime ethers I can form salts of alkali metal or alkaline earth metal compounds and also enol esters.

Alkali metal salts of the compounds I can be obtained by treating I with sodium hydroxide or alkoxide or potassium hydroxide or alkoxide in aqueous solution or in an organic solvent such as methanol, ethanol, acetone and toluene.

Other metal salts such as manganese, copper, zinc, iron, calcium, magnesium and barium salts can be prepared from the sodium salts in a customary manner, as well as ammonium, phosphonium, sulfonium or sulfoxonium salts by means of ammonia, or phosphonium, sulfonium or sulfoxonium hydroxides.

The esters of the compounds I are likewise obtainable in a customary manner (cf. eg. Organikum, VEB Deutscher Verlag der Wissenschaften, 17th Edition, Berlin 1988, pp. 405–408).

The 5-(sulfo-/carbamoylmethyl)cyclohexenone oxime ethers I can be obtained during preparation as an isomer mixture, both E/Z isomer mixtures (position of the oxime moiety —O-alk-phenyl relative to $R^1$) and enantiomer or diastereomer mixtures being possible. The isomer mixtures can be separated if desired by the methods customary for this purpose, eg. by chromatography or by crystallization.

The 5-(sulfo-/carbamoylmethyl)cyclohexenone oxime ethers I can be written in several tautomeric forms which are all encompassed by the invention:

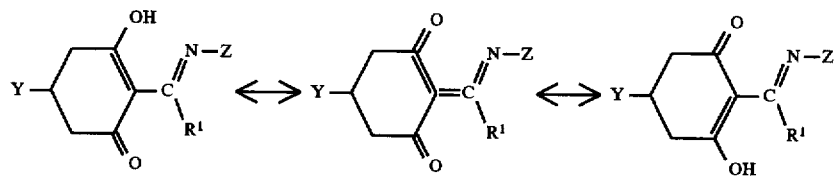

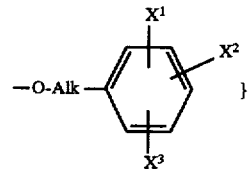

$\{Y=R^3-N(R^2)-CH_2-;\ Z=$ $\}$

The variables used in the definition of the 5-(sulfo-/carbamoylmethyl)cyclohexenone oxime ethers I specifically have the following meanings:

$R^1$ is $C_1$-$C_6$-alkyl such as methyl, ethyl, n-propyl, n-butyl, n-pentyl and n-hexyl, in particular ethyl or propyl;

$R^2$ is hydrogen;

$C_1$-$C_6$-alkyl such as methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 1,1-dimethylpropyl, 1,2-dimethylpropyl, 2,2-dimethylpropyl, 1-ethylpropyl, n-hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl 1-ethyl-1-methylpropyl and 1-ethyl-2-methylpropyl, in particular methyl, ethyl, n-propyl or 1-methylethyl;

$C_1$-$C_3$-alkyl such as methyl, ethyl, n-propyl and 1-methylethyl, the alkyl group being substituted by $C_1$-$C_3$-alkoxy such as methoxy, ethoxy, n-propoxy and 1-methylethoxy, that is eg. methoxymethyl, ethoxymethyl, n-propoxymethyl, (1-methylethoxy)methyl, 2-methoxyethyl, 2-ethoxyethyl, 2-(n-propoxy)ethyl, 2-(1-methylethoxy)ethyl, 2-(methoxy)propyl, 3-(methoxy)propyl, 2-(ethoxy)propyl, 3-(ethoxy)propyl and 3-propoxypropyl, in particular 2-methoxyethyl;

$C_3$-$C_6$-cycloalkyl such as cyclopropyl, cyclobutyl, cyclopentyl and cyclohexyl;

$R^3$ is $C_1$-$C_6$-alkylsulfonyl such as methylsulfonyl, ethylsulfonyl, n-propylsulfonyl, 1-methylethylsulfonyl, n-butylsulfonyl, 1-methylpropylsulfonyl, 2-methylpropylsulfonyl, 1,1-dimethylethylsulfonyl, n-pentylsulfonyl, 1-methylbutylsulfonyl, 2-methylbutylsulfonyl, 3-methylbutylsulfonyl, 1,1-dimethylpropylsulfonyl, 1,2-dimethylpropylsulfonyl, 2,2-dimethylpropylsulfonyl, 1-ethylpropylsulfonyl, n-hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl and 1-ethyl-2-methylpropylsulfonyl, in particular methylsulfonyl or ethylsulfonyl;

$C_1-C_6$-alkylcarbonyl such as methylcarbonyl, ethylcarbonyl, n-propylcarbonyl, 1-methylethylcarbonyl, n-butylcarbonyl, 1-methylpropylcarbonyl, 2-methylpropylcarbonyl, 1,1-dimethylethylcarbonyl, n-pentylcarbonyl, 1-methylbutylcarbonyl, 2-methylbutylcarbonyl, 3-methylbutylcarbonyl, 1,1-dimethylpropylcarbonyl, 1,2-dimethylpropylcarbonyl, 2,2-dimethylpropylcarbonyl, 1-ethylpropylcarbonyl, n-hexylcarbonyl, 1-methylpentylcarbonyl, 2-methylpentylcarbonyl, 3-methylpentylcarbonyl, 4-methylpentylcarbonyl, 1,1-dimethylbutylcarbonyl, 1,2-dimethylbutylcarbonyl, 1,3-dimethylbutylcarbonyl, 1-ethylbutylcarbonyl, 2-ethylbutylcarbonyl, 1,1,2-trimethylpropylcarbonyl, 1,2,2-trimethylpropylcarbonyl, 1-ethyl-1-methylpropylcarbonyl and 1-ethyl-2-methylpropylcarbonyl, in particular methylcarbonyl or ethylcarbonyl;

Alk is $C_2-C_4$-alkylene such as ethylene, propylene and butylene;

$C_3$- or $C_4$-alkenylene such as 2-propenylene, 2-butenylene and 3-butenylene;

$C_3$- or $C_4$-alkynylene such as 2-propynylene, 2-butynylene and 3-butynylene;

$C_2-C_3$-alkyleneoxy such as 2-ethyleneoxy, 2-propyleneoxy and 3-propyleneoxy;

it being possible for these chains if desired to carry a $C_1-C_3$-alkyl group such as methyl, ethyl, n-propyl, 1-methylethyl, in particular methyl;

$X^1$, $X^2$ and $X^3$ independently of one another are hydrogen;

halogen such as fluorine, chlorine, bromine and iodine, in particular fluorine or chlorine;

$C_1-C_4$-haloalkyl such as chloromethyl, dichloromethyl, trichloromethyl, fluoromethyl, difluoromethyl, trifluoromethyl, chlorofluoromethyl, chlorodifluoromethyl, dichlorofluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2-2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl and 1-(bromomethyl)-2-bromoethyl, in particular trifluoromethyl.

With respect to the herbicidal activity of the 5-(sulfamoylmethyl)cyclohexenones of the formula I, the following substituents, individually or in combination, are particularly preferred:

$R^2$ $C_1-C_6$-alkyl;

Alk butylene, 3-butenylene, 3-butynylene and $C_2-C_3$-alkyleneoxy;

$X^1$ hydrogen or halogen, in particular halogen;

$X^2$ halogen and $X^3$ hydrogen.

Suitable salts of the compounds of the formula I are agriculturally utilizable salts, for example alkali metal salts, in particular the sodium or potassium salts, alkaline earth metal salts, in particular the calcium, magnesium or barium salts, the manganese, copper, zinc or iron salts, and ammonium, phosphonium, sulfonium or sulfoxonium salts, for example ammonium salts, tetraalkylammonium salts, benzyltrialkylammonium salts, trialkylsulfonium salts or trialkylsulfoxonium salts.

Agriculturally utilizable esters are understood as meaning preferably the esters of $C_1-C_{10}$-fatty acids, in particular $C_1-C_6$-alkanecarboxylic acids such as methanecarboxylic acid (acetic acid), ethanecarboxylic acid (propionic acid), n-propanecarboxylic acid (butyric acid), 1-methylethanecarboxylic acid (isobutyric acid), n-butanecarboxylic acid, 1-methylpropanecarboxylic acid, 2-methylpropanecarboxylic acid, 1,1-dimethylethanecarboxylic acid, n-pentanecarboxylic acid, 1-methylbutane-carboxylic acid, 2-methylbutanecarboxylic acid, 3-methylbutane-carboxylic acid, 1,1-dimethylpropanecarboxylic acid, 1,2-dimethylpropanecarboxylic acid, 2,2-dimethylpropanecarboxylic acid, 1-ethylpropanecarboxylic acid, benzoic acid and benzoic acids substituted by halogen, n-hexanecarboxylic acid, 1-methylpentanecarboxylic acid, 2-methylpentanecarboxylic acid, 3-methylpentanecarboxylic acid, 4-methylpentanecarboxylic acid, 1,1-dimethylbutanecarboxylic acid, 1,2-dimethylbutanecarboxylic acid, 1,3-dimethylbutanecarboxylic acid, 2,2-dimethylbutanecarboxylic acid, 2,3-dimethylbutanecarboxylic acid, 3,3-dimethylbutanecarboxylic acid, 1-ethylbutanecarboxylic acid, 2-ethylbutanecarboxylic acid, 1,1,2-trimethylpropanecarboxylic acid, 1,2,2-trimethylpropanecarboxylic acid, 1ethyl-1-methylpropanecarboxylic acid and 1-ethyl-2-methylpropanecarboxylic acid.

The 5-(sulfo-/carbamoylmethyl)cyclohexenone oxime ethers I, their salts and esters are suitable, both as isomer mixtures and in the form of the pure isomers, as herbicides, in particular for controlling plant species from the grass family (Gramineae). In general, they are tolerable and thus selective in broad-leaved crops and in monocotyledonous plants which do not belong to the Gramineae. Some of the compounds I according to the invention are also suitable for the selective control of undesired grasses in Gramineae crops.

The selective action against weeds and grass weeds in crops such as wheat, rice, maize, soybeans and cotton occurs especially at low application rates.

The 5-(sulfo-/carbamoylmethyl)cyclohexenone oxime ethers I or the herbicidal compositions containing them can be applied by spraying, atomizing, dusting, broadcasting or watering in the form of directly sprayable aqueous solutions, powders, suspensions, even high-percentage aqueous, oily or other suspensions or dispersions, emulsions, oil dispersions, pastes, dusting compositions, broadcasting compositions or granules. The application forms depend on the intended uses; in each case if possible they should provide for extremely fine dispersion of the active ingredients according to the invention.

The compounds I are generally suitable for the production of directly sprayable solutions, emulsions, pastes or oil dispersions. Suitable inert additives are mineral oil fractions of medium to high boiling point, such as kerosene or diesel oil, and also coaltar oils and oils of vegetable or animal origin, aliphatic, cyclic and aromatic hydrocarbons, eg. paraffin, tetrahydronaphthalene, alkylated naphthalenes or their derivatives, alkylated benzenes or their derivatives, methanol, ethanol, propanol, butanol, cyclohexanol, cyclohexanone or strongly polar solvents, such as N-methylpyrrolidone or water.

Aqueous application forms can be prepared from emulsion concentrates, suspensions, pastes, wettable powders or water-dispersible granules by addition of water. To prepare emulsions, pastes or oil dispersions, the substrates as such or dissolved in an oil or solvent can be homogenized in water by means of wetting agents, adhesives, dispersants or emulsifiers. However, concentrates consisting of active ingredient, wetting agents, adhesives, dispersants or emulsifiers and possibly solvent or oil can also be prepared, which are suitable for dilution with water.

Suitable surface-active substances are the alkali metal, alkaline earth metal and ammonium salts of aromatic sulfonic acids. eg. lignosulfonic, phenolsulfonic, naphthalenesulfonic and dibutylnaphthalenesulfonic acid, as well as of fatty acids, alkyl- and alkylarylsulfonates, alkyl-, lauryl ether and fatty alcohol sulfates, and also salts of sulfated hexa-, hepta- and octadecanols and of fatty alcohol glycol ethers, condensation products of sulfonated naphthalene and its derivatives with formaldehyde, condensation products of naphthalene or of naphthalenesulfonic acids with phenol and formaldehyde, polyoxyethylene octylphenol ethers, ethoxylated isooctyl-, octyl- or nonylphenol, alkylphenyl or tributylphenyl polyglycol ethers, alkylaryl polyether alcohols, isotridecyl alcohol, fatty alcohol/ethylene oxide condensates, ethoxylated castor oil, polyoxyethylene or polyoxypropylene alkyl ethers, lauryl alcohol polyglycol ether acetate, sorbitol esters, lignin-sulfite waste liquors or methylcellulose.

Powder, broadcasting and dusting compositions can be prepared by mixing or joint grinding of the active substances with a solid carrier.

Granules, eg. coated, impregnated and homogeneous granules can be prepared by binding the active compounds to solid carriers. Solid carriers are mineral earths such as silicic acids, silica gel, silicates, talc, kaolin, limestone, lime, chalk, bole, loess, clay, dolomite, diatomaceous earth, calcium sulfate and magnesium sulfate, magnesium oxide, ground plastics, fertilizers such as ammonium sulfate, ammonium phosphate, ammonium nitrate, ureas and vegetable products such as cereal flour, tree bark meal, wood meal and nutshell meal, cellulose powder or other solid carriers.

The formulations in general contain from 0.01 to 95% by weight, preferably from 0.5 to 90% by weight, of at least one compound I. The active compounds are employed here in a purity of from 90% to 100%, preferably from 95% to 100% (according to NMR spectrum).

The compounds I according to the invention can be formulated, for example, as follows:

I. 20 parts by weight of the compound No. 1.02 are dissolved in a mixture which consists of 80 parts by weight of alkylated benzene, 10 parts by weight of the addition product of from 8 to 10 mol of ethylene oxide to 1 mol of oleic acid N-monoethanolamide, 5 parts by weight of calcium salt of dodecylbenzenesulfonic acid and 5 parts by weight of the addition product of 40 mol of ethylene oxide to 1 mol of castor oil. By pouring out the solution and finely dispersing it in 100,000 parts by weight of water, an aqueous dispersion is obtained which contains 0.02% by weight of the active ingredient.

II. 20 parts by weight of the compound No. 1.04 are dissolved in a mixture which consists of 40 parts by weight of cyclohexanone, 30 parts by weight of isobutanol, 20 parts by weight of the addition product of 7 mol of ethylene oxide to 1 mol of isooctylphenol and 10 parts by weight of the addition product of 40 mol of ethylene oxide to 1 mol of castor oil. By pouring the solution into and finely dispersing it in 100,000 parts by weight of water, an aqueous dispersion is obtained which contains 0.02% by weight of the active ingredient.

III. 20 parts by weight of the active ingredient No. 1.10 are dissolved in a mixture which consists of 25 parts by weight of cyclohexanone, 65 parts by weight of a mineral oil fraction of boiling point from 210° to 280° C. and 10 parts by weight of the addition product of 40 mol of ethylene oxide to 1 mol of castor oil. By pouring the solution into and finely dispersing it in 100,000 parts by weight of water, an aqueous dispersion is obtained which contains 0.02% by weight of the active ingredient.

IV. 20 parts by weight of the active ingredient No. 1.12 are well mixed with 3 parts by weight of the sodium salt of diisobutylnaphthalene-α-sulfonic acid, 17 parts by weight of the sodium salt of a lignosulfonic acid from a sulfite waste liquor and 60 parts by weight of powdered silica gel and ground in a hammer mill. By finely dispersing the mixture in 20,000 parts by weight of water, a spray mixture is obtained which contains 0.1% by weight of the active ingredient.

V. 3 parts by weight of the active ingredient No. 1.14 are mixed with 97 parts by weight of finely divided kaolin. In this manner, a dusting composition is obtained which contains 3% by weight of the active ingredient.

VI. 20 parts by weight of the active ingredient No. 1.22 are intimately mixed with 2 parts by weight of calcium salt of dodecylbenzenesulfonic acid, 8 parts by weight of fatty alcohol polyglycol ether, 2 parts by weight of sodium salt of a phenol/urea/formaldehyde condensate and 68 parts by weight of a paraffinic mineral oil. A stable oily dispersion is obtained.

The application of the herbicidal compositions or of the active ingredients can be carried out pre-emergence or post-emergence. If the active compounds are less tolerable for certain crop plants, application techniques can be used in which the herbicidal compositions are sprayed by means of the spray equipment such that if possible the leaves of the sensitive crop plants are as far as possible not affected, while the active compounds reach the leaves of undesired plants growing under them or the uncovered soil surface (post-directed, lay-by).

Depending on the target of control, time of year, target plants and growth stage, the application rates of active ingredient are from 0.001 to 3.0, preferably from 0.01 to 2.0, kg/ha of at least one active substance (a.s.) of the formula I.

Taking into account the variety of the application methods, the 5-(sulfo-/carbamoylmethyl)cyclohexenone oxime ethers I or compositions containing them can additionally be employed for the elimination of undesired plants in a further range of crop plants. Examples of suitable crops are the following:

*Allium cepa, Ananas comosus, Arachis hypogaea, Asparagus officinalis, Beta vulgaris* spp. *altissima, Beta vulgaris* spp. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragaria vesca, Glycine max, Gossypium hirsutum,* (*Gossypium arboreum, Gossypium herbaceum, Gossypium vitifolium*), *Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus* spp., *Manihot esculenta, Medicago sativa, Musa* spp., *Nicotiana tabacum* (*N.rustica*), *Olea europaea, Oryza sativa, Phaseolus lunatus, Phaseolus vulgaris, Picea abies, Pinus* spp., *Pisum sativum, Prunus avium, Prunus persica, Pyrus comunis, Ribes sylvestre, Ricinus communis, Saccharum officinarum, Secale cereale, Solanum tuberosum, Sorghum bicolor* (*S. vulgare*), *Theobroma cacao, Trifolium pratense, Triticum aestivum, Triticum durum, Vicia faba, Vitis vinifera, Zea mays.*

To broaden the spectrum of action and to achieve synergistic effects, the 5-(sulfo-/carbamoylmethyl)cyclohexenone oxime ethers I can be mixed and applied jointly with numerous representatives of other herbicidal or growth-regulating active compound groups. For example, suitable mixture components are diazines, 4H-3,1-benzoxazine derivatives, benzothiadiazinones, 2,6-dinitroanilines, N-phenylcarbamates, thiocarbamates, halocarboxylic acids, triazines, amides, ureas, diphenyl ethers, triazinones, uracils, benzofuran derivatives, cyclohexane-1,3-dione derivatives which carry eg. a carbonyl or carbimino group in the 2-position, quinolinecarboxylic acid derivatives, imidazolinones, sulfonamides, sulfonylureas, aryloxy- and heteroaryloxyphenoxypropionic acids and their salts, esters and amides and others.

It may additionally be of use to apply the compounds I on their own or jointly in combination with other herbicides also additionally mixed with further crop protection agents, for example with agents for controlling pests or phytopathogenic fungi or bacteria. Also of interest is the miscibility with inorganic salt solutions which are employed for eliminating nutritional and trace element deficiencies. Non-phytotoxic oils and oil concentrates can also be added.

PREPARATION EXAMPLES

Example 1

2-[1-{2-(4-Chlorophenoxy)propoxy]iminobutyl}-3-hydroxy-5-[(N-ethylsulfonyl-N-methylamino)methyl]-2-cyclohexen-1-one (Compound No. 1.04)

A mixture of 1.5 g (4.7 mmol) of 2-butyryl-3-hydroxy-5-[(N-ethylsulfonyl-N-methylamino)methyl]-2-cyclohexen-1-one and 1.2 g (5.9 mmol) of O-[2-(4-chlorophenoxy)propyl]hydroxylamine in 50 ml of methanol was stirred for 24 hours and then concentrated under reduced pressure. Workup to the product was carried out in the customary manner. Yield: 77% (oil);

$^1$H-NMR (200 MHz, in CDCl$_3$): see Table 2.

Example 2

2-(1-[2-(4-Fluorophenoxy)propoxy]iminopropyl)-3-hydroxy-5-[(N-ethylcarbonyl-N-methylamino)methyl]-2-cyclohexen-1-one (Compound No. 1.141)

A mixture of 1.35 g (5.0 mmol) of 3-hydroxy-5-[(N-ethylcarbonyl-N-methylamino)methyl]-2-propionyl-2-cyclohexen-1-one and 0.93 g (5.0 mmol) of O-[2-(4-fluorophenoxy)propyl]hydroxylamine in 20 ml of methanol was stirred for 24 hours and then concentrated under reduced pressure. Workup to the product was carried out in the customary manner. Yield: 2.1 g (oil). 1H-NMR see Table 2.

In the Table 1 below, further 5-(sulfo-/carbamoylmethyl) cyclohexenone oxime ethers I are listed which were prepared or can be prepared in the same manner. Physical data of compounds I are to be taken from Table 2.

TABLE 1

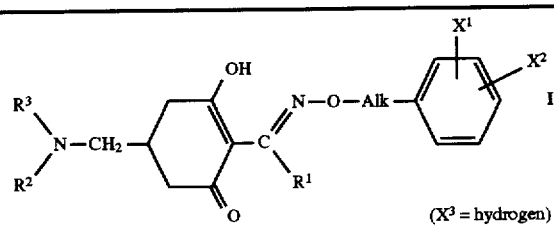

($X^3$ = hydrogen)

| No. | $R^1$ | $R^2$ | $R^3$ | Alk | $X^1$ | $X^2$ |
|---|---|---|---|---|---|---|
| 1.01 | Ethyl | Methyl | $H_3C-SO_2-$ | $-CH_2CH(CH_3)-O-$ | H | 4-Cl |
| 1.02 | Propyl | Methyl | $H_3C-SO_2-$ | $-CH_2CH(CH_3)-O-$ | H | 4-Cl |
| 1.03 | Ethyl | Methyl | $H_5C_2-SO_2-$ | $-CH_2CH(CH_3)-O-$ | H | 4-Cl |
| 1.04 | Propyl | Methyl | $H_5C_2-SO_2-$ | $-CH_2CH(CH_3)-O-$ | H | 4-Cl |
| 1.05 | Ethyl | Ethyl | $H_3C-SO_2-$ | $-CH_2CH(CH_3)-O-$ | H | 4-Cl |
| 1.06 | Propyl | Ethyl | $H_3C-SO_2-$ | $-CH_2CH(CH_3)-O-$ | H | 4-Cl |
| 1.07 | Ethyl | Ethyl | $H_5C_2-SO_2-$ | $-CH_2CH(CH_3)-O-$ | H | 4-Cl |
| 1.08 | Propyl | Ethyl | $H_5C_2-SO_2-$ | $-CH_2CH(CH_3)-O-$ | H | 4-Cl |
| 1.09 | Ethyl | 2-Methoxy-ethyl | $H_3C-SO_2-$ | $-CH_2CH(CH_3)-O-$ | H | 4-Cl |
| 1.10 | Propyl | 2-Methoxy-ethyl | $H_3C-SO_2-$ | $-CH_2CH(CH_3)-O-$ | H | 4-Cl |
| 1.11 | Ethyl | 1-Methyl-ethyl | $H_3C-SO_2-$ | $-CH_2CH(CH_3)-O-$ | H | 4-Cl |

TABLE 1-continued

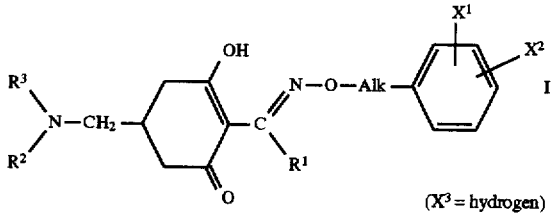

($X^3$ = hydrogen)

| No. | $R^1$ | $R^2$ | $R^3$ | Alk | $X^1$ | $X^2$ |
|---|---|---|---|---|---|---|
| 1.12 | Propyl | 1-Methyl-ethyl | $H_3C-SO_2-$ | $-CH_2CH(CH_3)-O-$ | H | 4-Cl |
| 1.13 | Ethyl | n-Propyl | $H_3C-SO_2-$ | $-CH_2CH(CH_3)-O-$ | H | 4-Cl |
| 1.14 | Propyl | n-Propyl | $H_3C-SO_2-$ | $-CH_2CH(CH_3)-O-$ | H | 4-Cl |
| 1.15 | Ethyl | n-Butyl | $H_3C-SO_2-$ | $-CH_2CH(CH_3)-O-$ | H | 4-Cl |
| 1.16 | Propyl | n-Butyl | $H_3C-SO_2-$ | $-CH_2CH(CH_3)-O-$ | H | 4-Cl |
| 1.17 | Ethyl | 2-Methyl-propyl | $H_3C-SO_2-$ | $-CH_2CH(CH_3)-O-$ | H | 4-Cl |
| 1.18 | Propyl | 2-Methyl-propyl | $H_3C-SO_2-$ | $-CH_2CH(CH_3)-O-$ | H | 4-Cl |
| 1.19 | Ethyl | Cyclo-pentyl | $H_3C-SO_2-$ | $-CH_2CH(CH_3)-O-$ | H | 4-Cl |
| 1.20 | Propyl | Cyclo-pentyl | $H_3C-SO_2-$ | $-CH_2CH(CH_3)-O-$ | H | 4-Cl |
| 1.21 | Ethyl | Cyclo-hexyl | $H_3C-SO_2-$ | $-CH_2CH(CH_3)-O-$ | H | 4-Cl |
| 1.22 | Propyl | Cyclo-hexyl | $H_3C-SO_2-$ | $-CH_2CH(CH_3)-O-$ | H | 4-Cl |
| 1.23 | Ethyl | Methyl | $H_3C-SO_2-$ | $-CH_2CH(CH_3)-O-$ | H | 4-F |
| 1.24 | Propyl | Methyl | $H_3C-SO_2-$ | $-CH_2CH(CH_3)-O-$ | H | 4-F |
| 1.25 | Ethyl | Methyl | $H_5C_2-SO_2-$ | $-CH_2CH(CH_3)-O-$ | H | 4-F |
| 1.26 | Propyl | Methyl | $H_5C_2-SO_2-$ | $-CH_2CH(CH_3)-O-$ | H | 4-F |
| 1.27 | Ethyl | Ethyl | $H_3C-SO_2-$ | $-CH_2CH(CH_3)-O-$ | H | 4-F |
| 1.28 | Propyl | Ethyl | $H_3C-SO_2-$ | $-CH_2CH(CH_3)-O-$ | H | 4-F |
| 1.29 | Ethyl | Ethyl | $H_5C_2-SO_2-$ | $-CH_2CH(CH_3)-O-$ | H | 4-F |
| 1.30 | Propyl | Ethyl | $H_5C_2-SO_2-$ | $-CH_2CH(CH_3)-O-$ | H | 4-F |
| 1.31 | Ethyl | Methyl | $H_3C-SO_2-$ | $-CH_2CH(CH_3)-O-$ | 2-Cl | 4-Cl |
| 1.32 | Propyl | Methyl | $H_3C-SO_2-$ | $-CH_2CH(CH_3)-O-$ | 2-Cl | 4-Cl |
| 1.33 | Ethyl | Methyl | $H_5C_2-SO_2-$ | $-CH_2CH(CH_3)-O-$ | 2-Cl | 4-Cl |
| 1.34 | Propyl | Methyl | $H_5C_2-SO_2-$ | $-CH_2CH(CH_3)-O-$ | 2-Cl | 4-Cl |
| 1.35 | Ethyl | Ethyl | $H_3C-SO_2-$ | $-CH_2CH(CH_3)-O-$ | 2-Cl | 4-Cl |
| 1.36 | Propyl | Ethyl | $H_3C-SO_2-$ | $-CH_2CH(CH_3)-O-$ | 2-Cl | 4-Cl |
| 1.37 | Ethyl | Ethyl | $H_5C_2-SO_2-$ | $-CH_2CH(CH_3)-O-$ | 2-Cl | 4-Cl |
| 1.38 | Propyl | Ethyl | $H_5C_2-SO_2-$ | $-CH_2CH(CH_3)-O-$ | 2-Cl | 4-Cl |
| 1.39 | Ethyl | Methyl | $H_3C-SO_2-$ | $-CH_2CH(CH_3)-O-$ | 2-F | 4-F |
| 1.40 | Propyl | Methyl | $H_5C_2-SO_2-$ | $-CH_2CH(CH_3)-O-$ | 2-F | 4-F |
| 1.41 | Ethyl | Methyl | $H_5C_2-SO_2-$ | $-CH_2CH(CH_3)-O-$ | 2-F | 4-F |
| 1.42 | Propyl | Methyl | $H_5C_2-SO_2-$ | $-CH_2CH(CH_3)-O-$ | 2-F | 4-F |
| 1.43 | Ethyl | Ethyl | $H_3C-SO_2-$ | $-CH_2CH(CH_3)-O-$ | 2-F | 4-F |
| 1.44 | Propyl | Ethyl | $H_3C-SO_2-$ | $-CH_2CH(CH_3)-O-$ | 2-F- | 4-F |
| 1.45 | Ethyl | Ethyl | $H_5C_2-SO_2-$ | $-CH_2CH(CH_3)-O-$ | 2-F | 4-F |
| 1.46 | Propyl | Ethyl | $H_5C_2-SO_2-$ | $-CH_2CH(CH_3)-O-$ | 2-F | 4-F |
| 1.47 | Ethyl | Methyl | $H_3C-SO_2-$ | $-CH_2CH_2-O-$ | 2-Cl | 4-Cl |
| 1.48 | Propyl | Methyl | $H_3C-SO_2-$ | $-CH_2CH_2-O-$ | 2-Cl | 4-Cl |
| 1.49 | Ethyl | Methyl | $H_5C_2-SO_2-$ | $-CH_2CH_2-O-$ | 2-Cl | 4-Cl |
| 1.50 | Propyl | Methyl | $H_5C_2-SO_2-$ | $-CH_2CH_2-O-$ | 2-Cl | 4-Cl |
| 1.51 | Ethyl | Ethyl | $H_3C-SO_2-$ | $-CH_2CH_2-O-$ | 2-Cl | 4-Cl |
| 1.52 | Propyl | Ethyl | $H_3C-SO_2-$ | $-CH_2CH_2-O-$ | 2-Cl | 4-Cl |
| 1.53 | Ethyl | Ethyl | $H_5C_2-SO_2-$ | $-CH_2CH_2-O-$ | 2-Cl | 4-Cl |
| 1.54 | Propyl | Ethyl | $H_5C_2-SO_2-$ | $-CH_2CH_2-O-$ | 2-Cl | 4-Cl |
| 1.55 | Ethyl | Methyl | $H_3C-SO_2-$ | $-CH_2CH_2-O-$ | 2-F | 4-F |
| 1.56 | Propyl | Methyl | $H_3C-SO_2-$ | $-CH_2CH_2-O-$ | 2-F | 4-F |
| 1.57 | Ethyl | Methyl | $H_5C_2-SO_2-$ | $-CH_2CH_2-O-$ | 2-F | 4-F |
| 1.58 | Propyl | Methyl | $H_5C_2-SO_2-$ | $-CH_2CH_2-O-$ | 2-F | 4-F |
| 1.59 | Ethyl | Ethyl | $H_3C-SO_2-$ | $-CH_2CH_2-O-$ | 2-F | 4-F |
| 1.60 | Propyl | Ethyl | $H_3C-SO_2-$ | $-CH_2CH_2-O-$ | 2-F | 4-F |
| 1.61 | Ethyl | Ethyl | $H_5C_2-SO_2-$ | $-CH_2CH_2-O-$ | 2-F | 4-F |
| 1.62 | Propyl | Ethyl | $H_5C_2-SO_2-$ | $-CH_2CH_2-O-$ | 2-F | 4-F |
| 1.63 | Ethyl | Methyl | $H_3C-SO_2-$ | $-CH_2CH_2-O-$ | H | 4-$CF_3$ |
| 1.64 | Propyl | Methyl | $H_3C-SO_2-$ | $-CH_2CH_2-O-$ | H | 4-$CF_3$ |
| 1.65 | Ethyl | Methyl | $H_5C_2-SO_2-$ | $-CH_2CH_2-O-$ | H | 4-$CF_3$ |
| 1.66 | Propyl | Methyl | $H_5C_2-SO_2-$ | $-CH_2CH_2-O-$ | H | 4-$CF_3$ |
| 1.67 | Ethyl | Ethyl | $H_3C-SO_2-$ | $-CH_2CH_2-O-$ | H | 4-$CF_3$ |
| 1.68 | Propyl | Ethyl | $H_3C-SO_2-$ | $-CH_2CH_2-O-$ | H | 4-$CF_3$ |
| 1.69 | Ethyl | Ethyl | $H_5C_2-SO_2-$ | $-CH_2CH_2-O-$ | H | 4-$CF_3$ |
| 1.70 | Propyl | Ethyl | $H_5C_2-SO_2-$ | $-CH_2CH_2-O-$ | H | 4-$CF_3$ |

TABLE 1-continued

[Structure I: cyclohexenone with OH, N-O-Alk-phenyl(X¹,X²) substituents, R³R²N-CH₂-, R¹ group] (X³ = hydrogen)

| No. | R¹ | R² | R³ | Alk | X¹ | X² |
|---|---|---|---|---|---|---|
| 1.71 | Ethyl | Methyl | H₃C—SO₂— | —CH₂CH₂CH₂—O— | 2-F | 4-F |
| 1.72 | Propyl | Methyl | H₃C—SO₂— | —CH₂CH₂CH₂—O— | 2-F | 4-F |
| 1.73 | Ethyl | Methyl | H₅C₂—SO₂— | —CH₂CH₂CH₂—O— | 2-F | 4-F |
| 1.74 | Propyl | Methyl | H₅C₂—SO₂— | —CH₂CH₂CH₂—O— | 2-F | 4-F |
| 1.75 | Ethyl | Ethyl | H₃C—SO₂— | —CH₂CH₂CH₂—O— | 2-F | 4-F |
| 1.76 | Propyl | Ethyl | H₃C—SO₂— | —CH₂CH₂CH₂—O— | 2-F | 4-F |
| 1.77 | Ethyl | Ethyl | H₅C₂—SO₂— | —CH₂CH₂CH₂—O— | 2-F | 4-F |
| 1.78 | Propyl | Ethyl | H₅C₂—SO₂— | —CH₂CH₂CH₂—O— | 2-F | 4-F |
| 1.79 | Ethyl | Methyl | H₃C—SO₂— | —CH₂CH₂CH₂CH₂— | H | 4-F |
| 1.80 | Propyl | Methyl | H₃C—SO₂— | —CH₂CH₂CH₂CH₂— | H | 4-F |
| 1.81 | Ethyl | Methyl | H₅C₂—SO₂— | —CH₂CH₂CH₂CH₂— | H | 4-F |
| 1.82 | Propyl | Methyl | H₅C₂—SO₂— | —CH₂CH₂CH₂CH₂— | H | 4-F |
| 1.83 | Ethyl | Ethyl | H₃C—SO₂— | —CH₂CH₂CH₂CH₂— | H | 4-F |
| 1.84 | Propyl | Ethyl | H₃C—SO₂— | —CH₂CH₂CH₂CH₂— | H | 4-F |
| 1.85 | Ethyl | Ethyl | H₅C₂—SO₂— | —CH₂CH₂CH₂CH₂— | H | 4-F |
| 1.86 | Propyl | Ethyl | H₅C₂—SO₂— | —CH₂CH₂CH₂CH₂— | H | 4-F |
| 1.87 | Ethyl | Methyl | H₃C—SO₂— | —CH₂CH₂CH=CH— | H | 4-Cl |
| 1.88 | Propyl | Methyl | H₃C—SO₂— | —CH₂CH₂CH=CH— | H | 4-Cl |
| 1.89 | Ethyl | Methyl | H₅C₂—SO₂— | —CH₂CH₂CH=CH— | H | 4-Cl |
| 1.90 | Propyl | Methyl | H₅C₂—SO₂— | —CH₂CH₂CH=CH— | H | 4-Cl |
| 1.91 | Ethyl | Ethyl | H₃C—SO₂— | —CH₂CH₂CH=CH— | H | 4-Cl |
| 1.92 | Propyl | Ethyl | H₃C—SO₂— | —CH₂CH₂CH=CH— | H | 4-Cl |
| 1.93 | Ethyl | Ethyl | H₅C₂—SO₂— | —CH₂CH₂CH=CH— | H | 4-Cl |
| 1.94 | Propyl | Ethyl | H₅C₂—SO₂— | —CH₂CH₂CH=CH— | H | 4-Cl |
| 1.95 | Ethyl | Methyl | H₃C—SO₂— | —CH₂CH₂CH=CH— | H | 4-F |
| 1.96 | Propyl | Methyl | H₃C—SO₂— | —CH₂CH₂CH=CH— | H | 4-F |
| 1.97 | Ethyl | Methyl | H₅C₂—SO₂— | —CH₂CH₂CH=CH— | H | 4-F |
| 1.98 | Propyl | Methyl | H₅C₂—SO₂— | —CH₂CH₂CH=CH— | H | 4-F |
| 1.99 | Ethyl | Ethyl | H₃C—SO₂— | —CH₂CH₂CH=CH— | H | 4-F |
| 1.100 | Propyl | Ethyl | H₃C—SO₂— | —CH₂CH₂CH=CH— | H | 4-F |
| 1.101 | Ethyl | Ethyl | H₅C₂—SO₂— | —CH₂CH₂CH=CH— | H | 4-F |
| 1.102 | Propyl | Ethyl | H₅C₂—SO₂— | —CH₂CH₂CH=CH— | H | 4-F |
| 1.103 | Ethyl | Methyl | H₃C—SO₂— | —CH₂CH₂C≡C— | H | 4-F |
| 1.104 | Propyl | Methyl | H₃C—SO₂— | —CH₂CH₂C≡C— | H | 4-F |
| 1.105 | Ethyl | Methyl | H₅C₂—SO₂— | —CH₂CH₂C≡C— | H | 4-F |
| 1.106 | Propyl | Methyl | H₅C₂—SO₂— | —CH₂CH₂C≡C— | H | 4-F |
| 1.107 | Ethyl | Ethyl | H₃C—SO₂— | —CH₂CH₂C≡C— | H | 4-F |
| 1.108 | Propyl | Ethyl | H₃C—SO₂— | —CH₂CH₂C≡C— | H | 4-F |
| 1.109 | Ethyl | Ethyl | H₅C₂—SO₂— | —CH₂CH₂C≡C— | H | 4-F |
| 1.110 | Propyl | Ethyl | H₅C₂—SO₂— | —CH₂CH₂C≡C— | H | 4-F |
| 1.111 | Propyl | n-Butyl | H₃C—SO₂— | —CH₂CH(CH₃)—O— | H | 4-Cl |
| 1.112 | Propyl | Cyclopentyl | H₃C—SO₂— | —CH₂CH(CH₃)—O— | H | 4-Cl |
| 1.113 | Propyl | 2-Methylpropyl | H₃C—SO₂— | —CH₂CH(CH₃)—O— | H | 4-Cl |
| 1.114 | Propyl | Methyl | H₅C₂—SO₂— | —CH₂CH(CH₃)—O— | 3-Cl | 5-Cl |
| 1.115 | Ethyl | Methyl | H₅C₂—SO₂— | —CH₂CH(CH₃)—O— | 3-Cl | 5-Cl |
| 1.116 | Ethyl | Methyl | H₅C₂—SO₂— | —CH₂— | H | 3-Cl |
| 1.117 | Ethyl | Methyl | H₃C—CO— | —CH₂CH(CH₃)—O— | H | 4-Cl |
| 1.118 | Propyl | Methyl | H₃C—CO— | —CH₂CH(CH₃)—O— | H | 4-Cl |
| 1.119 | Ethyl | Methyl | H₅C₂—CO— | —CH₂CH(CH₃)—O— | H | 4-Cl |
| 1.120 | Propyl | Methyl | H₅C₂—CO— | —CH₂CH(CH₃)—O— | H | 4-Cl |
| 1.121 | Ethyl | Ethyl | H₃C—CO— | —CH₂CH(CH₃)—O— | H | 4-Cl |
| 1.122 | Propyl | Ethyl | H₃C—CO— | —CH₂CH(CH₃)—O— | H | 4-Cl |
| 1.123 | Ethyl | Ethyl | H₅C₂—CO— | —CH₂CH(CH₃)—O— | H | 4-Cl |
| 1.124 | Propyl | Ethyl | H₅C₂—CO— | —CH₂CH(CH₃)—O— | H | 4-Cl |
| 1.125 | Ethyl | 2-Methoxyethyl | H₃C—CO— | —CH₂CH(CH₃)—O— | H | 4-Cl |
| 1.126 | Propyl | 2-Methoxyethyl | H₃C—CO— | —CH₂CH(CH₃)—O— | H | 4-Cl |

TABLE 1-continued $(X^3 = \text{hydrogen})$

| No. | $R^1$ | $R^2$ | $R^3$ | Alk | $X^1$ | $X^2$ |
|---|---|---|---|---|---|---|
| 1.127 | Ethyl | 1-Methyl-ethyl | $H_3C-CO-$ | $-CH_2CH(CH_3)-O-$ | H | 4-Cl |
| 1.128 | Propyl | 1-Methyl-ethyl | $H_3C-CO-$ | $-CH_2CH(CH_3)-O-$ | H | 4-Cl |
| 1.129 | Ethyl | n-Propyl | $H_3C-CO-$ | $-CH_2CH(CH_3)-O-$ | H | 4-Cl |
| 1.130 | Propyl | n-Propyl | $H_3C-CO-$ | $-CH_2CH(CH_3)-O-$ | H | 4-Cl |
| 1.131 | Ethyl | n-Butyl | $H_3C-CO-$ | $-CH_2CH(CH_3)-O-$ | H | 4-Cl |
| 1.132 | Propyl | n-Butyl | $H_3C-CO-$ | $-CH_2CH(CH_3)-O-$ | H | 4-Cl |
| 1.133 | Ethyl | 2-Methyl-propyl | $H_3C-CO-$ | $-CH_2CH(CH_3)-O-$ | H | 4-Cl |
| 1.134 | Propyl | 2-Methyl-propyl | $H_3C-CO-$ | $-CH_2CH(CH_3)-O-$ | H | 4-Cl |
| 1.135 | Ethyl | Cyclo-pentyl | $H_3C-CO-$ | $-CH_2CH(CH_3)-O-$ | H | 4-Cl |
| 1.136 | Propyl | Cyclo-pentyl | $H_3C-CO-$ | $-CH_2CH(CH_3)-O-$ | H | 4-Cl |
| 1.137 | Ethyl | Cyclo-hexyl | $H_3C-CO-$ | $-CH_2CH(CH_3)-O-$ | H | 4-Cl |
| 1.138 | Propyl | Cyclo-hexyl | $H_3C-CO-$ | $-CH_2CH(CH_3)-O-$ | H | 4-Cl |
| 1.139 | Ethyl | Methyl | $H_3C-CO-$ | $-CH_2CH(CH_3)-O-$ | H | 4-F |
| 1.140 | Propyl | Methyl | $H_3C-CO-$ | $-CH_2CH(CH_3)-O-$ | H | 4-F |
| 1.141 | Ethyl | Methyl | $H_5C_2-CO-$ | $-CH_2CH(CH_3)-O-$ | H | 4-F |
| 1.142 | Propyl | Methyl | $H_5C_2-CO-$ | $-CH_2CH(CH_3)-O-$ | H | 4-F |
| 1.143 | Ethyl | Ethyl | $H_3C-CO-$ | $-CH_2CH(CH_3)-O-$ | H | 4-F |
| 1.144 | Propyl | Ethyl | $H_3C-CO-$ | $-CH_2CH(CH_3)-O-$ | H | 4-F |
| 1.145 | Ethyl | Ethyl | $H_5C_2-CO-$ | $-CH_2CH(CH_3)-O-$ | H | 4-F |
| 1.146 | Propyl | Ethyl | $H_5C_2-CO-$ | $-CH_2CH(CH_3)-O-$ | H | 4-F |
| 1.147 | Ethyl | Methyl | $H_3C-CO-$ | $-CH_2CH(CH_3)-O-$ | 2-Cl | 4-Cl |
| 1.148 | Propyl | Methyl | $H_3C-CO-$ | $-CH_2CH(CH_3)-O-$ | 2-Cl | 4-Cl |
| 1.149 | Ethyl | Methyl | $H_5C_2-CO-$ | $-CH_2CH(CH_3)-O-$ | 2-Cl | 4-Cl |
| 1.150 | Propyl | Methyl | $H_5C_2-CO-$ | $-CH_2CH(CH_3)-O-$ | 2-Cl | 4-Cl |
| 1.151 | Ethyl | Ethyl | $H_3C-CO-$ | $-CH_2CH(CH_3)-O-$ | 2-Cl | 4-Cl |
| 1.152 | Propyl | Ethyl | $H_3C-CO-$ | $-CH_2CH(CH_3)-O-$ | 2-Cl | 4-Cl |
| 1.153 | Ethyl | Ethyl | $H_5C_2-CO-$ | $-CH_2CH(CH_3)-O-$ | 2-Cl | 4-Cl |
| 1.154 | Propyl | Ethyl | $H_5C_2-CO-$ | $-CH_2CH(CH_3)-O-$ | 2-Cl | 4-Cl |
| 1.155 | Ethyl | Methyl | $H_3C-CO-$ | $-CH_2CH(CH_3)-O-$ | 2-F | 4-F |
| 1.156 | Propyl | Methyl | $H_3C-CO-$ | $-CH_2CH(CH_3)-O-$ | 2-F | 4-F |
| 1.157 | Ethyl | Methyl | $H_5C_2-CO-$ | $-CH_2CH(CH_3)-O-$ | 2-F | 4-F |
| 1.158 | Propyl | Methyl | $H_5C_2-CO-$ | $-CH_2CH(CH_3)-O-$ | 2-F | 4-F |
| 1.159 | Ethyl | Ethyl | $H_3C-CO-$ | $-CH_2CH(CH_3)-O-$ | 2-F | 4-F |
| 1.160 | Propyl | Ethyl | $H_3C-CO-$ | $-CH_2CH(CH_3)-O-$ | 2-F | 4-F |
| 1.161 | Ethyl | Ethyl | $H_5C_2-CO-$ | $-CH_2CH(CH_3)-O-$ | 2-F | 4-F |
| 1.162 | Propyl | Ethyl | $H_5C_2-CO-$ | $-CH_2CH(CH_3)-O-$ | 2-F | 4-F |
| 1.163 | Ethyl | Methyl | $H_3C-CO-$ | $-CH_2CH_2-O-$ | 2-Cl | 4-Cl |
| 1.164 | Propyl | Methyl | $H_3C-CO-$ | $-CH_2CH_2-O-$ | 2-Cl | 4-Cl |
| 1.165 | Ethyl | Methyl | $H_5C_2-CO-$ | $-CH_2CH_2-O-$ | 2-Cl | 4-Cl |
| 1.166 | Propyl | Methyl | $H_5C_2-CO-$ | $-CH_2CH_2-O-$ | 2-Cl | 4-Cl |
| 1.167 | Ethyl | Ethyl | $H_3C-CO-$ | $-CH_2CH_2-O-$ | 2-Cl | 4-Cl |
| 1.168 | Propyl | Ethyl | $H_3C-CO-$ | $-CH_2CH_2-O-$ | 2-Cl | 4-Cl |
| 1.169 | Ethyl | Ethyl | $H_5C_2-CO-$ | $-CH_2CH_2-O-$ | 2-Cl | 4-Cl |
| 1.170 | Propyl | Ethyl | $H_5C_2-CO-$ | $-CH_2CH_2-O-$ | 2-Cl | 4-Cl |
| 1.171 | Ethyl | Methyl | $H_3C-CO-$ | $-CH_2CH_2-O-$ | 2-F | 4-F |
| 1.172 | Propyl | Methyl | $H_3C-CO-$ | $-CH_2CH_2-O-$ | 2-F | 4-F |
| 1.173 | Ethyl | Methyl | $H_5C_2-CO-$ | $-CH_2CH_2-O-$ | 2-F | 4-F |
| 1.174 | Propyl | Methyl | $H_5C_2-CO-$ | $-CH_2CH_2-O-$ | 2-F | 4-F |
| 1.175 | Ethyl | Ethyl | $H_3C-CO-$ | $-CH_2CH_2-O-$ | 2-F | 4-F |
| 1.176 | Propyl | Ethyl | $H_3C-CO-$ | $-CH_2CH_2-O-$ | 2-F | 4-F |
| 1.177 | Ethyl | Ethyl | $H_5C_2-CO-$ | $-CH_2CH_2-O-$ | 2-F | 4-F |
| 1.178 | Propyl | Ethyl | $H_5C_2-CO-$ | $-CH_2CH_2-O-$ | 2-F | 4-F |
| 1.179 | Ethyl | Methyl | $H_3C-CO-$ | $-CH_2CH_2-O-$ | H | 4-$CF_3$ |
| 1.180 | Propyl | Methyl | $H_3C-CO-$ | $-CH_2CH_2-O-$ | H | 4-$CF_3$ |
| 1.181 | Ethyl | Methyl | $H_5C_2-CO-$ | $-CH_2CH_2-O-$ | H | 4-$CF_3$ |
| 1.182 | Propyl | Methyl | $H_5C_2-CO-$ | $-CH_2CH_2-O-$ | H | 4-$CF_3$ |
| 1.183 | Ethyl | Ethyl | $H_3C-CO-$ | $-CH_2CH_2-O-$ | H | 4-$CF_3$ |

TABLE 1-continued

Structure I: Cyclohexenone with OH, N-O-Alk-phenyl(X1,X2), R1, R2R3N-CH2- substituents (X3 = hydrogen)

| No. | R1 | R2 | R3 | Alk | X1 | X2 |
|---|---|---|---|---|---|---|
| 1.184 | Propyl | Ethyl | $H_3C-CO-$ | $-CH_2CH_2-O-$ | H | 4-$CF_3$ |
| 1.185 | Ethyl | Ethyl | $H_5C_2-CO-$ | $-CH_2CH_2-O-$ | H | 4-$CF_3$ |
| 1.186 | Propyl | Ethyl | $H_5C_2-CO-$ | $-CH_2CH_2-O-$ | H | 4-$CF_3$ |
| 1.187 | Ethyl | Methyl | $H_3C-CO-$ | $-CH_2CH_2CH_2-O-$ | 2-F | 4-F |
| 1.188 | Propyl | Methyl | $H_3C-CO-$ | $-CH_2CH_2CH_2-O-$ | 2-F | 4-F |
| 1.189 | Ethyl | Methyl | $H_5C_2-CO-$ | $-CH_2CH_2CH_2-O-$ | 2-F | 4-F |
| 1.190 | propyl | Methyl | $H_5C_2-CO-$ | $-CH_2CH_2CH_2-O-$ | 2-F | 4-F |
| 1.191 | Ethyl | Ethyl | $H_3C-CO-$ | $-CH_2CH_2CH_2-O-$ | 2-F | 4-F |
| 1.192 | Propyl | Ethyl | $H_3C-CO-$ | $-CH_2CH_2CH_2-O-$ | 2-F | 4-F |
| 1.193 | Ethyl | Ethyl | $H_5C_2-CO-$ | $-CH_2CH_2CH_2-O-$ | 2-F | 4-F |
| 1.194 | Propyl | Ethyl | $H_5C_2-CO-$ | $-CH_2CH_2CH_2-O-$ | 2-F | 4-F |
| 1.195 | Ethyl | Methyl | $H_3C-CO-$ | $-CH_2CH_2CH_2CH_2-$ | H | 4-F |
| 1.196 | Propyl | Methyl | $H_3C-CO-$ | $-CH_2CH_2CH_2CH_2-$ | H | 4-F |
| 1.197 | Ethyl | Methyl | $H_5C_2-CO-$ | $-CH_2CH_2CH_2CH_2-$ | H | 4-F |
| 1.198 | Propyl | Methyl | $H_5C_2-CO-$ | $-CH_2CH_2CH_2CH_2-$ | H | 4-F |
| 1.199 | Ethyl | Ethyl | $H_3C-CO-$ | $-CH_2CH_2CH_2CH_2-$ | H | 4-F |
| 1.200 | Propyl | Ethyl | $H_3C-CO-$ | $-CH_2CH_2CH_2CH_2-$ | H | 4-F |
| 1.201 | Ethyl | Ethyl | $H_5C_2-CO-$ | $-CH_2CH_2CH_2CH_2-$ | H | 4-F |
| 1.202 | Propyl | Ethyl | $H_5C_2-CO-$ | $-CH_2CH_2CH_2CH_2-$ | H | 4-F |
| 1.203 | Ethyl | Methyl | $H_3C-CO-$ | $-CH_2CH_2CH=CH-$ | H | 4-Cl |
| 1.204 | Propyl | Methyl | $H_3C-CO-$ | $-CH_2CH_2CH=CH-$ | H | 4-Cl |
| 1.205 | Ethyl | Methyl | $H_5C_2-CO-$ | $-CH_2CH_2CH=CH-$ | H | 4-Cl |
| 1.206 | Propyl | Methyl | $H_5C_2-CO-$ | $-CH_2CH_2CH=CH-$ | H | 4-Cl |
| 1.207 | Ethyl | Ethyl | $H_3C-CO-$ | $-CH_2CH_2CH=CH-$ | H | 4-Cl |
| 1.208 | Propyl | Ethyl | $H_3C-CO-$ | $-CH_2CH_2CH=CH-$ | H | 4-Cl |
| 1.209 | Ethyl | Ethyl | $H_5C_2-CO-$ | $-CH_2CH_2CH=CH-$ | H | 4-Cl |
| 1.210 | Propyl | Ethyl | $H_5C_2-CO-$ | $-CH_2CH_2CH=CH-$ | H | 4-Cl |
| 1.211 | Ethyl | Methyl | $H_3C-CO-$ | $-CH_2CH_2CH=CH-$ | H | 4-F |
| 1.212 | Propyl | Methyl | $H_3C-CO-$ | $-CH_2CH_2CH=CH-$ | H | 4-F |
| 1.213 | Ethyl | Methyl | $H_5C_2-CO-$ | $-CH_2CH_2CH=CH-$ | H | 4-F |
| 1.214 | Propyl | Methyl | $H_5C_2-CO-$ | $-CH_2CH_2CH=CH-$ | H | 4-F |
| 1.215 | Ethyl | Ethyl | $H_3C-CO-$ | $-CH_2CH_2CH=CH-$ | H | 4-F |
| 1.216 | Propyl | Ethyl | $H_3C-CO-$ | $-CH_2CH_2CH=CH-$ | H | 4-F |
| 1.217 | Ethyl | Ethyl | $H_5C_2-CO-$ | $-CH_2CH_2CH=CH-$ | H | 4-F |
| 1.218 | Propyl | Ethyl | $H_5C_2-CO-$ | $-CH_2CH_2CH=CH-$ | H | 4-F |
| 1.219 | Ethyl | Methyl | $H_3C-CO-$ | $-CH_2CH_2C\equiv C-$ | H | 4-F |
| 1.220 | Propyl | Methyl | $H_3C-CO-$ | $-CH_2CH_2C\equiv C-$ | H | 4-F |
| 1.221 | Ethyl | Methyl | $H_5C_2-CO-$ | $-CH_2CH_2C\equiv C-$ | H | 4-F |
| 1.222 | Propyl | Methyl | $H_5C_2-CO-$ | $-CH_2CH_2C\equiv C-$ | H | 4-F |
| 1.223 | Ethyl | Ethyl | $H_3C-CO-$ | $-CH_2CH_2C\equiv C-$ | H | 4-F |
| 1.224 | Propyl | Ethyl | $H_3C-CO-$ | $-CH_2CH_2C\equiv C-$ | H | 4-F |
| 1.225 | Ethyl | Ethyl | $H_5C_2-CO-$ | $-CH_2CH_2C\equiv C-$ | H | 4-F |
| 1.226 | Propyl | Ethyl | $H_5C_2-CO-$ | $-CH_2CH_2C\equiv C-$ | H | 4-F |
| 1.227 | Ethyl | Methyl | $H_5C_2-CO-$ | $-CH_2CH(CH_3)-O-$ | 3-Cl | 5-Cl |

TABLE 2

| No. | Physical Data ($^1$H-NMR: δ [ppm]) |
|---|---|
| 1.02 | 2.80(s, 3H), 2.90(s, 3H), 4.20(m, 2H), 4.60(m, 1H), 6.85(m, 2H), 7.25(m, 2H) |
| 1.03 | 1.1(m, 3H), 1.3(m, 6H), 4.2(m, 2H), 4.6(m, 1H), 6.8(m, 2H), 7.2(m, 2H) |
| 1.04 | 2.90(s, 3H), 4.20(m, 2H), 4.60(m, 1H), 6.85(m, 2H), 7.25(m, 2H) |
| 1.10 | 2.90(s, 3H), 3.35(s, 3H), 4.15(m, 2H), 4.60(m, 1H), 6.85(m, 2H), 7.20(m, 2H) |
| 1.12 | 2.85(s, 3H), 4.20(m, 2H), 4.60(m, 1H), 6.85(m, 2H), 7.25(m, 2H) |
| 1.14 | 2.85(s, 3H), 4.15(m, 2H), 4.60(m, 1H), 6.85(d, 2H), 7.20(d, 2H) |
| 1.22 | 2.85(s, 3H), 4.20(m, 2H), 4.60(m, 1H), 6.85(m, 2H), 7.20(d, 2H) |

TABLE 2-continued

| No. | Physical Data ($^1$H-NMR: δ [ppm]) |
|---|---|
| 1.25 | 1.1(m, 3H), 1.3(m, 6H), 2.9(s, 3H), 4.2(m, 2H), 4.5(m, 1H), 6.8(m, 4H) |
| 1.26 | 2.9(m, 3H), 4.2(m, 2H), 4.6(m, 1H), 6.9(m, 4H) |
| 1.33 | 1.1(m, 3H), 1.3(m, 6H), 2.9(s, 3H), 4.2(m, 2H), 4.6(m, 1H), 6.9(d, 1H), 7.2(m, 1H), 7.3(m, 1H) |
| 1.34 | 1.35(m, 6H), 1.5(m, 2H), 2.6(m, 2H), 2.8(m, 2H), 2.9(s, 3H), 4.2(m, 2H), 4.6(m, 1H), 6.1(m, 1H), 7.15(m, 1H), 7.35(m, 1H) |
| 1.41 | 1.1(m, 3H), 1.3(m, 6H), 2.9(s, 3H), 4.2(m, 2H), 4.5(m, 1H), 6.8(m, 2H), 7.0(m, 1H) |
| 1.42 | 1.3(m, 6H), 2.9(s, 3H), 4.2(m, 2H), 4.5(m, 1H), 6.7(m, 3H) |
| 1.111 | 1.6(m, 4H), 2.8(s, 3H), 6.9(m, 2H), 7.2(m, 2H) |
| 1.112 | 1.3(m, 2H), 2.8(s, 3H), 6.9(m, 2H), 7.1(m, 2H) |
| 1.113 | 1.3(m, 3H), 2.8(m, 3H), 6.9(m, 2H), 7.2(m, 2H) |
| 1.114 | 1.4(m, 3H), 2.9(s, 3H), 4.2(m, 2H), 4.7(m, 1H), 6.9(m, 2H), 7.0(m, 1H) |
| 1.115 | 1.1(t, 3H), 1.3(m, 3H), 2.9(s, 3H), 4.2(m, 2H), 4.6(m, 1H), 6.8(d, 2H), 6.9(m, 1H) |
| 1.116 | 1.1(m, 3H), 1.3(m, 3H), 2.9(s, 3H), 3.0(m, 2H), 3.1(m, 2H), 5.0(s, 2H), 7.2(m, 4H) |
| 1.119 | 1.10(t), 1.15(t), 1.33(d), 3.01(s), 4.62(m), 6.84(d), 7.22(d) |
| 1.120 | 0.90(t), 1.15(t), 1.35(d), 3.00(s), 4.63(m), 6.85(d), 7.24(d) |
| 1.141 | 1.15(t), 1.34(d), 3.01(s), 4.58(m), 6.80–7.05(m) |
| 1.149 | 1.16(t), 1.40(d), 3.02(s), 4.63(m), 6.92(d), 7.17(dd), 7.37(d) |
| 1.157 | 1.13(t), 1.33(d), 3.02(s), 4.52(m), 6.70–7.10(m) |
| 1.227 | 1.15(t), 1.35(d), 3.02(s), 4.63(m), 6.83(s), 6.95(s) |

Use Examples

It was possible to show the herbicidal action of the 5-(sulfo-/carbamoylmethyl)cyclohexenone oxime ethers of the formula I by greenhouse tests:

The cultivation pots used were plastic flowerpots containing loamy sand with about 3.0% humus as a substrate. The seeds of the test plants were sown separately according to species.

In the case of pre-emergence treatment, the active compounds suspended or emulsified in water were applied directly after sowing by means of finely dispersing nozzles. The pots were lightly watered in order to promote germination and growth, and then covered with transparent plastic hoods until the plants had taken root. This covering caused uniform germination of the test plants if this was not impaired by the active compounds.

For the purpose of post-emergence treatment, the test plants were first raised, depending on growth form, to a height of growth of from 3 to 15 cm and only then treated with the active ingredients suspended or emulsified in water. The test plants were either sown directly for this purpose and raised in the same containers or they were first raised separately as seedlings and transplanted into the experimental pots a few days before treatment.

The application rates for the post-emergence treatment was 0.25, 0.125 or 0.06 kg/ha of active ingredient (a.s.).

The plants were kept in a species-specific manner at 10°–25° C. or 20°–35C. The test period extended over 2 to 4 weeks. During this time the plants were tended and their reaction to the separate treatments was assessed.

Assessment was carried out on a scale of from 0 to 100. 100 here means no emergence of the plants or complete destruction of at least the above-ground parts and 0 means no damage or normal course of growth.

The plants used in the greenhouse tests were made up of the following species:

| Botanical name | Common name |
|---|---|
| Echinochloa crusgalli | barnyard grass |
| Oryza sativa | rice |
| Setaria faberii | giant foxtail |
| Setaria viridis | green foxtail |

The result showed that undesired grasses in rice as example crop can be very well controlled using the compounds Nos. 1.04 and 1.149. A compound disclosed in WO 92/08696 (Table 1, No. 1.22) and also tested for comparison $$C_2H_5-SO_2 \diagdown N-CH_2-\!\!\!\!\bigcirc\!\!\!\!-C(=N-O-CH_2-CH=CH_2)-CH_2-C_2H_5$$
(with OH and =O substituents on cyclohexenone ring)

in contrast also damaged the crop plants to an untolerably high extent in addition to the grass weeds.

We claim:

1. A 5-(sulfo-/carbamoylmethyl) cyclohexenone oxime ether of the formula I $$\text{I: } R^3\text{-N}(R^2)\text{-CH}_2\text{-[cyclohexenone with OH]-C}(R^1)\text{=N-O-Alk-[phenyl with }X^1, X^2, X^3\text{]}$$

where the variables have the following meanings:
  R$^1$ is C$_1$–C$_6$-alkyl;
  R$^2$ is hydrogen, C$_1$–C$_6$-alkyl, C$_1$–C$_3$-alkoxy-C$_1$–C$_3$-alkyl or C$_3$–C$_6$-cycloalkyl;
  R$^3$ is C$_1$–C$_4$-alkylsulfonyl or C$_1$–C$_4$-alkylcarbonyl;
  Alk is [a C$_2$–C$_4$-alkylene chain, a C$_3$- or C$_4$-alkenylene chain, a C$_3$- or C$_4$alkynylene chain, a] an unsubstituted C$_2$- or C$_3$-alkyleneoxy chain or a C$_2$- or C$_3$-alkyleneoxy chain bearing a C$_1$–C$_3$-alkyl group;
  X$^1$, X$^2$ and X$^3$ independently of one another are hydrogen, halogen or C$_1$–C$_4$-haloalkyl,
and the agriculturally utilizable salts of I and the esters of I with C$_1$–C$_{10}$-carboxylic acids or inorganic acids.

2. A herbicidal composition containing at least one inert liquid and/or solid carrier and, optionally, at least one adjuvant and also a herbicidally active amount of at least one 5-(sulfo-/carbamoylmethyl)cyclohexenone oxime ether of the formula I or a salt or an ester of I, as defined in claim 1.

3. A process for preparing herbicidally active compositions, which comprises mixing a herbicidally active amount of at least one 5-(sulfo-/carbamoylmethyl) cyclohexenone oxime ether of the formula I or of a salt or ester of I, as claimed in claim 1, and at least one liquid and/or solid carrier and also, optionally, at least one adjuvant.

4. A method for controlling undesired plant growth, which comprises allowing a herbicidally active amount of at least one 5-(sulfo-/carbamoylmethyl)cyclohexenone oxime ether of the formula I or of a salt or ester of I, as defined in claim 1, to act on plants, their habitat or on seed.

5. An oxime ether of the formula I as defined in claim 1, wherein $R^1$ is ethyl or propyl,
$R^2$ is methyl or ethyl,
$R^3$ is $H_3C-CO-$ or $H_5C_2-CO-$,
Alk is $-CH(CH_3)-O-$,
$X^1$ is 2-Cl,
$X^2$ is 4-Cl, and
$X^3$ is hydrogen.

6. An oxime ether of the formula I as defined in claim 1 wherein
$R^1$ is ethyl,
$R^2$ is methyl,
$R^3$ is $H_5C_2-CO-$,
Alk is $-CH_2CH(CH_3)-O-$,
$X^1$ is 2-Cl,
$X^2$ is 4-Cl, and
$X^3$ is hydrogen.

7. An oxime ether of the formula I as defined in claim 1, wherein
$R^1$ is propyl,
$R^2$ is methyl,
$R^3$ is $H_5C_2-SO_2-$,
Alk is $-CH_2CH(CH_3)-O-$,
$X^1$ is hydrogen,
$X^2$ is 4-Cl, and
$X_3$ is hydrogen.

* * * * *

UNITED STATES PATENT AND TRADEMARK OFFICE
CERTIFICATE OF CORRECTION

PATENT NO.: 5,674,812

DATED: October 7, 1997

INVENTOR(S): MISSLITZ et al.

It is certified that error appears in the above-identified patent and that said Letters Patent is hereby corrected as shown below:

Column 20, claim 1, lines 42 and 43, delete "[a $C_2$-$C_4$-alkylene chain, a $C_3$- or $C_4$-alkenylene chain, a $C_3$- or $C_4$alkynylene chain, a]".

Signed and Sealed this

Sixteenth Day of December, 1997

Attest:

BRUCE LEHMAN

*Attesting Officer*     Commissioner of Patents and Trademarks